(12) United States Patent
Dring et al.

(10) Patent No.: US 9,925,550 B2
(45) Date of Patent: Mar. 27, 2018

(54) ARTICLES PROVIDING LONG LASTING FRAGRANCES

(71) Applicant: The Procter & Gamble Company, Cincinnati, OH (US)

(72) Inventors: Neil Charles Dring, Medmenham (GB); Lee Burrowes, Horsell (GB); Elaine Alice Marie Baxter, Twickenham (GB); Madhuri Jayant Khanolkar, Singapore (SG); Julien Claude Plos, London (GB); Alastair Robert Edward MacGregor, Egham (GB); Jiten Odhavji Dihora, Liberty Township, OH (US); Adam Gaszton Horvath, West Drayton (GB); Zerlina Guzdar Dubois, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 202 days.

(21) Appl. No.: 14/734,151

(22) Filed: Jun. 9, 2015

(65) Prior Publication Data

US 2015/0352575 A1    Dec. 10, 2015

Related U.S. Application Data

(60) Provisional application No. 62/009,382, filed on Jun. 9, 2014.

(51) Int. Cl.
| | | |
|---|---|---|
| *B05B 11/00* | (2006.01) | |
| *A45D 34/04* | (2006.01) | |
| *A61L 2/22* | (2006.01) | |

(52) U.S. Cl.
CPC .......... *B05B 11/3084* (2013.01); *A45D 34/04* (2013.01); *A61L 2/22* (2013.01); *B05B 11/3001* (2013.01); *B05B 11/3047* (2013.01)

(58) Field of Classification Search
CPC ....... A45D 34/04; A61L 2/22; B05B 11/3001; B05B 11/3047; B05B 11/3084
See application file for complete search history.

(56) References Cited

U.S. PATENT DOCUMENTS

| | | |
|---|---|---|
| 2,800,458 A | 6/1953 | Green |
| 2,730,456 A | 1/1956 | Green et al. |

(Continued)

FOREIGN PATENT DOCUMENTS

| | | |
|---|---|---|
| CA | 2735761 | 1/2012 |
| CN | 201537558 | 8/2010 |

(Continued)

OTHER PUBLICATIONS

Patchan, et al., Liquid-Filled Metal Microcapsules, ACS Appl. Mater. Interfaces, vol. 4, pp. 2406-2412, 2012.

(Continued)

*Primary Examiner* — J. Casimer Jacyna
*Assistant Examiner* — Bob Zadeh
(74) *Attorney, Agent, or Firm* — Betty J. Zea

(57) ABSTRACT

A dispenser comprising a first reservoir in liquid communication with a first pump; a second reservoir in liquid communication with a second pump; exit orifice; and an actuator; wherein the first and second pumps are in liquid communication with the exit orifice; wherein the second pump is in liquid communication with the exit orifice; wherein said first and second pumps are in communication with the actuator; wherein the first reservoir comprises a first composition, comprising a volatile solvent and a first fragrance; wherein the second reservoir comprises a second composition, comprising a carrier and a plurality of microcapsules; wherein the exit orifice dispenses a first dose of the first composition and a second dose of the second composition; wherein the microcapsules have a volume weighted (Continued)

fracture strength from about 0.1 Mpa to about 25 Mpa, and a median volume-weighted particle size from about 2 microns to about 80 microns.

15 Claims, 2 Drawing Sheets

(56) References Cited

U.S. PATENT DOCUMENTS

| | | |
|---|---|---|
| 2,800,457 A | 7/1957 | Green et al. |
| 4,552,811 A | 11/1985 | Brown et al. |
| 5,152,431 A | 10/1992 | Gardner et al. |
| 5,169,029 A | 12/1992 | Behar et al. |
| 5,398,846 A | 3/1995 | Corba et al. |
| 5,402,916 A | 4/1995 | Nottingham et al. |
| 5,482,188 A | 1/1996 | Lina |
| 5,535,950 A | 7/1996 | Barriac et al. |
| 5,803,318 A | 9/1998 | Lina |
| 5,826,048 A | 10/1998 | Dempsey et al. |
| 5,836,479 A | 11/1998 | Klima et al. |
| 5,967,372 A | 10/1999 | Favre |
| 5,971,210 A | 10/1999 | Brugger |
| 6,454,315 B1 | 9/2002 | Brozell |
| 6,592,990 B2 | 7/2003 | Schwantes |
| 7,335,631 B2 | 2/2008 | McDermott et al. |
| 7,819,342 B2 | 10/2010 | Spallek et al. |
| 9,102,898 B2 | 8/2015 | Barone |
| 9,364,838 B2 | 6/2016 | Parmentier |
| 2003/0215417 A1 | 11/2003 | Ichiyama et al. |
| 2005/0092778 A1 | 5/2005 | Bistolfi |
| 2005/0113282 A1 | 5/2005 | Parekh et al. |
| 2005/0150905 A1 | 7/2005 | Van Der Heijden et al. |
| 2005/0226900 A1 | 10/2005 | Brooks et al. |
| 2005/0242118 A1* | 11/2005 | Van der Heijden ...... B05B 11/0048 222/137 |
| 2006/0102656 A1* | 5/2006 | Troost .................. A61K 8/11 222/132 |
| 2006/0205617 A1 | 9/2006 | Holzner et al. |
| 2006/0258768 A1 | 11/2006 | Nara et al. |
| 2008/0118568 A1* | 5/2008 | Smets .................. A61K 8/8152 424/489 |
| 2009/0258812 A1* | 10/2009 | Sengupta ............... A61K 8/042 510/475 |
| 2009/0274906 A1* | 11/2009 | Schwantes ............ B01J 13/16 428/402.22 |
| 2010/0108779 A1 | 5/2010 | Filsouf |
| 2011/0268802 A1 | 11/2011 | Dihora et al. |
| 2012/0276175 A1* | 11/2012 | Dihora .................. A61K 8/11 424/401 |
| 2012/0279990 A1 | 11/2012 | Werner et al. |
| 2014/0086965 A1* | 3/2014 | Dihora .............. C11D 17/0039 424/401 |
| 2014/0178442 A1 | 6/2014 | Li et al. |
| 2014/0326753 A1 | 11/2014 | Turner |
| 2015/0071976 A1 | 3/2015 | Dihora et al. |
| 2015/0352575 A1* | 12/2015 | Dring .................. B05B 11/3084 222/137 |

FOREIGN PATENT DOCUMENTS

| | | |
|---|---|---|
| EP | 0676339 | 10/1995 |
| EP | 1184071 | 3/2002 |
| EP | 1359212 A1 | 11/2003 |
| EP | 1176945 B1 | 3/2004 |
| FR | 1408299 | 8/1965 |
| GB | 1182520 | 2/1970 |
| JP | 4464803 | 5/2010 |
| WO | WO 2015/031418 A1 | 3/2015 |

OTHER PUBLICATIONS

PCT International Search Report dated Sep. 24, 2015—11 pages.
PCT International Search Report dated Sep. 21, 2015—11 pages.
PCT International Search Report dated Sep. 21, 2015—10 pages.
PCT International Search Report dated Nov. 4, 2015—14 pages.
PCT International Search Report dated Aug. 19, 2015—9 pages.
PCT International Search Report dated Sep. 16, 2015—8 pages.
PCT International Search Report dated Sep. 15, 2015—9 pages.
All Office Action U.S. Appl. No. 14/734,180.
All Office Action U.S. Appl. No. 14/734,199.
All Office Action U.S. Appl. No. 14/734,234.
All Office Action U.S. Appl. No. 14/734,348.
All Office Action U.S. Appl. No. 14/734,429.
All Office Action U.S. Appl. No. 14/734,462.
All Office Action U.S. Appl. No. 14/734,512.
All Office Action U.S. Appl. No. 14/734,588.
All Office Action U.S. Appl. No. 14/734,673.
Zhang, Z. et al., "Mechanical Strength of Single Microcapsules Determined by a Novel Micromanipulation Technique," J. Microencapsulation, vol. 16, No. 1, pp. 117-124, 1999.
Sun, G. and Zhang, Z., "Mechanical Properties of Melamine-Formaldehyde Microcapsules," J. Microencapsulation, vol. 18, No. 5, pp. 593-602, 2001.
U.S. Appl. No. 14/734,180, filed Jun. 9, 2015, Dring, et al.
U.S. Appl. No. 14/734,199, filed Jun. 9, 2015, Dring, et al.
U.S. Appl. No. 14/734,234, filed Jun. 9, 2015, Burrowes, et al.
U.S. Appl. No. 14/734,348, filed Jun. 9, 2015, Burrowes, et al.
U.S. Appl. No. 14/734,429, filed Jun. 9, 2015, Burrowes, et al.
U.S. Appl. No. 14/734,462, filed Jun. 9, 2015, Burrowes, et al.
U.S. Appl. No. 14/734,512, filed Jun. 9, 2015, Burrowes, et al.
U.S. Appl. No. 14/734,588, filed Jun. 9, 2015, Burrowes, et al.
U.S. Appl. No. 14/734,673, filed Jun. 9, 2015, Burrowes, et al.

* cited by examiner

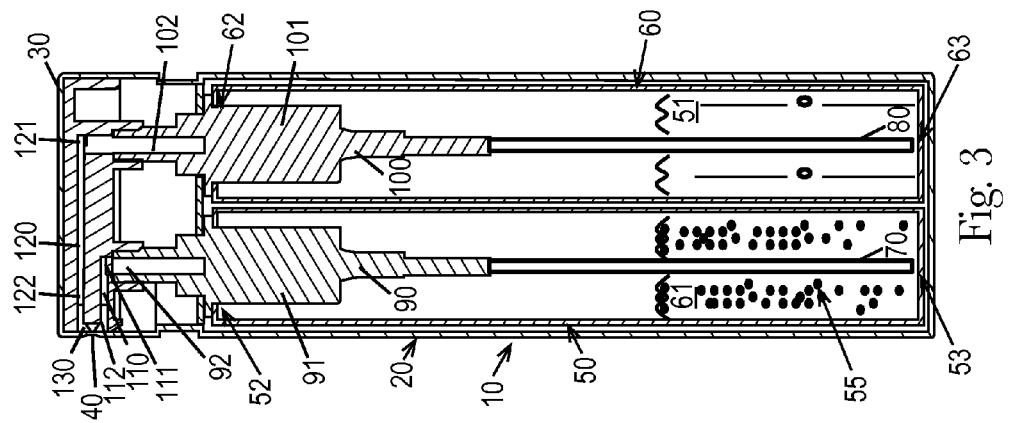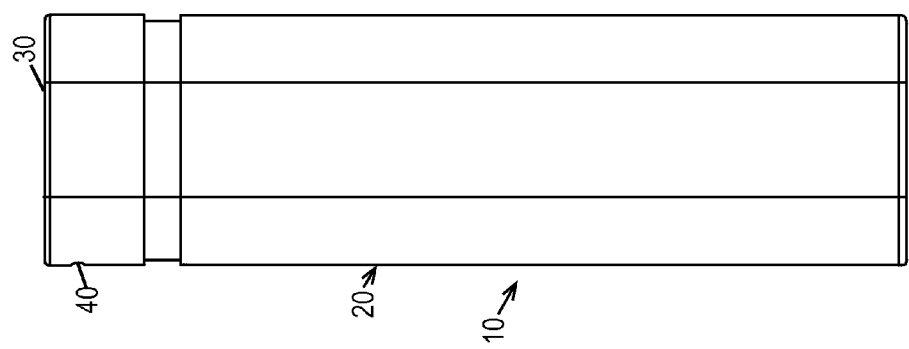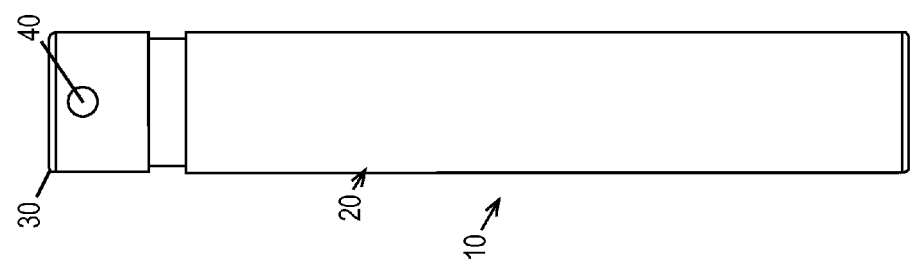

ARTICLES PROVIDING LONG LASTING FRAGRANCES

TECHNICAL FIELD

The present disclosure generally relates to articles and methods for dispensing a dose of two compositions, wherein at least one of the compositions includes microcapsules containing a fragrance.

BACKGROUND

Consumers often desire to deliver pleasant fragrances during and/or after application of a product. In fact, it is known that even ancient Egyptians utilized fragrances for their own personal enjoyment. Such fragrances often contain perfume oils and/or other odoriferous materials that provide a scent for a limited period of time. The limited period of noticeability for fragrances is typically a result of the volatility of the fragrance. In order to compensate for the limited period of noticeability of fragrances, it is not uncommon for some consumers to spray a fragrance multiple times during the day in order to extend the period of noticeability. This reapplication may not be desirable to consumers as they may be required to carry containers of fine fragrance about their person to perform the reapplication during the day. Thus, there exists a need for products that can deliver fragrances with a longer duration of noticeability.

SUMMARY

A dispenser comprising: a first reservoir in liquid communication with a first pump, the first pump comprising a first piston; a second reservoir in liquid communication with a second pump, the second pump comprising a second piston; at least one exit orifice; and an actuator; wherein the first pump is in liquid communication with the at least one exit orifice; wherein the second pump is in liquid communication with the at least one exit orifice; wherein said first and second pistons are in communication with the actuator; wherein the first reservoir comprises the first composition, the first composition comprising a volatile solvent and a first fragrance; wherein the second reservoir comprises the second composition, the second composition comprising a carrier and a plurality of microcapsules; wherein the at least one exit orifice dispenses a first dose of the first composition and a second dose of the second composition.

A method of providing a longer lasting fragrance, the method comprising applying to a situs a mixture of a first composition and a second composition using a dispenser comprising: a first reservoir in liquid communication with a first pump, the first pump comprising a first piston; a second reservoir in liquid communication with a second pump, the second pump comprising a second piston; at least one exit orifice; and an actuator; wherein the first pump is in communication with the at least one exit orifice; wherein the second pump is in communication with the at least one exit orifice; wherein said first and second pistons are in communication with the actuator; wherein the first reservoir comprises the first composition, the first composition comprising a volatile solvent and a first fragrance; wherein the second reservoir comprises the second composition, the second composition comprising a carrier and a plurality of microcapsules; wherein the at least one exit orifice dispenses a first dose of the first composition and a second dose of the second composition.

BRIEF DESCRIPTION OF THE DRAWINGS

While the specification concludes with claims, it is believed that the same will be better understood from the following description taken in conjunction with the accompanying drawings in which:
FIG. 1 is a front view of a dispenser;
FIG. 2 is a side view of a dispenser;
FIG. 3 is a cross sectional view of the side of a dispenser.

DETAILED DESCRIPTION

Figure 4:
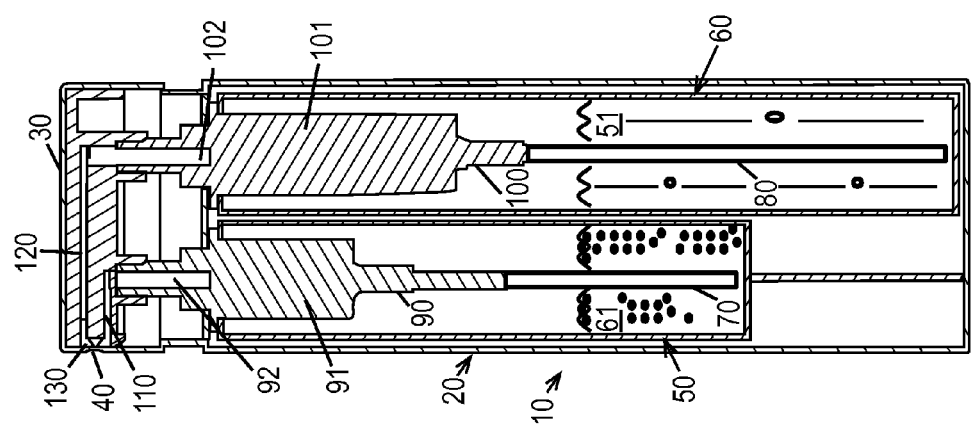
FIG. 4 is a cross sectional view of the side of a dispenser.

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Composition" as used herein, means ingredients suitable for topical application on mammalian keratinous tissue. Such compositions may also be suitable for application to textiles or any other form of clothing including, but not limited to, clothing made from synthetic fibers like nylons and polyesters, and clothing made from acetate, bamboo, cupro, hemp, flannel, jute, lyocell, PVC-polyvinyl chloride, rayon, recycled materials, rubber, soy, Tyvek, cotton, and other natural fibers.

"Free of" means that the stated ingredient has not been added to the composition. However, the stated ingredient may incidentally form as a byproduct or a reaction product of the other components of the composition.

"Nonvolatile" refers to those materials that liquid or solid under ambient conditions and have a measurable vapor pressure at 25° C. These materials typically have a vapor pressure of less than about 0.0000001 mmHg, and an average boiling point typically greater than about 250° C.

"Soluble" means at least about 0.1 g of solute dissolves in 100 ml of solvent at 25° C. and 1 atm of pressure.

"Substantially free of" means an amount of a material that is less than 1%, 0.5%, 0.25%, 0.1%, 0.05%, 0.01%, or 0.001% by weight of a composition.

"Derivatives" as used herein, include but are not limited to, amide, ether, ester, amino, carboxyl, acetyl, and/or alcohol derivatives of a given chemical.

"Skin care actives" as used herein, means substances that when applied to the skin, provide a benefit or improvement to the skin. It is to be understood that skin care actives are useful not only for application to skin, but also to hair, nails and other mammalian keratinous tissue.

"Situs" means the location where the composition is applied. Non-limiting examples of a situs include mammalian keratinous tissue and clothing.

"Volatile," as used herein, unless otherwise specified, refers to those materials that are liquid or SOLID under ambient conditions and which have a measurable vapor pressure at 25° C. These materials typically have a vapor pressure of greater than about 0.0000001 mmHg, alternatively from about 0.02 mmHg to about 20 mmHg, and an average boiling point typically less than about 250° C., alternatively less than about 235° C.

Perfumers often select odoriferous materials to blend into a composition with the goal of achieving an overall specific fragrance with a particular strength and character. In so doing, the perfumer may take into account the individual character and volatility of the odoriferous materials when forming the fragrance. Conventional compositions may often have a fragrance characterized by a higher amount of the less volatile odoriferous materials and lower amounts of the more volatile odoriferous materials. The less volatile odoriferous materials are commonly referred to as "base notes", while the more volatile odoriferous materials can be further divided into highly volatile odoriferous materials, identified as "top notes", and intermediate volatile odoriferous materials, identified as "middle notes."

To date, due to the volatility of the odoriferous materials, the types of fragrance available are limited. In this regard, perfumers often blend top notes, middle notes, and base notes to deliver a particular fragrance profile over time. Perfumers may use top notes to deliver the initial impression of the fragrance, yet may not rely on the top notes to contribute to the overall fragrance profile over time. Middle notes generally become the dominant scent to the untrained nose from several minutes after application and may last up to a few hours after application. Base notes may not be perceived as the dominant scent until several hours after the application of the fragrance or during the "dry-down" period. Base notes may be included to improve the noticeability of the fragrance over time and to replace the middle notes as the middle notes decline. However, if base notes are reduced or excluded from the fragrance, the noticeability of the fragrance may prematurely diminish over time.

Common complaints by users of fragrances include that the middle notes fade too quickly after application of the fragrance and that the character of the middle notes are undesirably altered by the presence of large amounts of the base notes during the period known as the "dry-down" phase. To overcome these complaints, users may resort to self-remedies by reapplying their fragrance throughout the day in order to achieve a fresh burst of top and/or middle notes for delight and noticability. However, reapplication of the fragrance during the day may not be desirable as this may require the dispenser containing the fragrance to be readily available to the user during use. It is therefore a challenge to formulate a composition having improved longevity and noticability of the fragrance character without substantially altering the character of the fragrance.

One method known to increase the duration of noticeability of a fragrance in a product is to incorporate a controlled-release system into a product. In this regard, microcapsules have been included in certain products like deodorants in order to delay the release of the fragrance into the headspace. While microcapsules have existed since the 1950s, there are no known products on the market that contain microcapsules in a composition that also includes ethanol at levels typically found in fine fragrances or that deliver microcapsules in combination with a volatile solvent like ethanol.

As shown in Table 1 below, the presence of volatile solvents like ethanol in a composition can cause fragrance-loaded microcapsules, such as those whose shells contain a polyacrylate material, to prematurely release the encapsulated fragrance. This loss was as high as 60% after a five day incubation at room temperature.

TABLE 1

| Type of Composition | % Leakage |
|---|---|
| Ethanol/Water (3:1 ratio) | >60% after 5 days at room temperature |

While it may be possible to include fragrance-loaded microcapsules in a fine fragrance devoid of a volatile solvent, fine fragrances typically include a volatile solvent for the benefits the volatile solvent may provide. For example, the volatile solvent may be used to solubilize a hydrophobic fragrance. Second, the volatile solvent may act as an invisible carrier for the fragrance as the volatile solvent may quickly evaporate after application and may not leave a visible or tactile residue on the skin and/or clothing. Third, the volatile solvent may enhance the noticeability of the solubilized fragrance upon evaporation. Therefore, it may be desirable to include a volatile solvent in a fine fragrance in addition to fragrance-loaded microcapsules. In this regard, the microcapsules may be used to deliver top and middle notes for an extended period of time, not only increasing the duration of the fragrance, but allowing the perfumer to alter that character of the fragrance over time.

When the stability of an ingredient is compromised by inclusion in a product base, a potential solution is to separate the ingredient from the product base by using a container with separate reservoirs for storing the incompatible ingredients. However, separating the microcapsules from the ethanol-containing composition until dispensing may still not lead to a consumer noticeable benefit because (1) the microcapsules and ethanol will either mix at the point of dispensing or immediately prior to dispensing, depending on the design of the dispenser and (2) the microcapsules and ethanol mixture are typically allowed to dry on the situs. Thus, due to the exquisite sensitivity of the microcapsules to the volatile solvent, the fragrance-loaded microcapsules may not survive intact after application when mixed with a volatile solvent like ethanol even though the microcapsules and volatile solvent are contained separately.

Additionally, if the dispenser aerosolizes the microcapsules included in the fine fragrance, the microcapsules must be resilient enough to survive the actuation force and other forces that are applied to the microcapsule during the spraying process as the use of fine fragrances typically involves spraying the fine fragrance onto a situs like a forearm, neck, or garment. For example, the microcapsule's shell would need to be strong enough to allow for the microcapsule to survive the travel from the reservoir to the situs without pre-maturely releasing the core material, yet weak enough so that the microcapsule can still release its core material during normal human movements. Furthermore, enough microcapsules must survive the spraying process such that a noticeable longevity benefit is provided after each use.

Surprisingly, it has been discovered that minimizing the contact time between the microcapsules and the volatile solvent (e.g. ethanol) may allow the microcapsules to deliver a noticeable benefit to a consumer. In some examples, a dispenser may be designed such that the dispenser includes a first reservoir and a second reservoir. The first reservoir may include a first composition comprising a volatile solvent and at least one fragrance. The second reservoir may include second composition comprising a plurality of microcapsules encapsulating a fragrance, a suspending agent, and a carrier. The dispenser may be designed to dispense a first dose of the first composition and a second dose of the second composition and may mix the two compositions before exiting the dispenser and/or in-flight.

Alternatively, two dispensers for application may be used such that one dispenser is used to contain and spray a first composition and the second is used to contain and spray a second composition. In this format, the first composition may include a volatile solvent and a fragrance and the second composition may include a carrier and a plurality of microcapsules encapsulating a fragrance. Said dispensers may be sold as a kit, the kit containing the two dispensers, and optionally, advertised as providing a longer lasting fragrance.

Surprisingly, it has also been discovered that microcapsules with a fracture strength from about 0.1 MPa to about 25.0 MPa may survive the dispenser's spraying process and may rupture during human movements such that a fragrance benefit is provided. As shown in Table 2, a dispenser comprising Composition A, a dispenser comprising Composition B, and a dispenser comprising C were evaluated for their ability to deliver a consumer noticeable fragrance benefit as described below under Consumer Test Protocol I. Composition A included a volatile solvent and a fragrance, and is further described below in Example 2. Composition B included water, and is further described below in Example 2. Composition C included water, a suspending agent, and microcapsules encapsulating a fragrance, and is further described below in Example 2. As shown in Table 2, panelists receiving a dose of Composition A and Composition C attributed a significantly higher score at all time points tested as compared to those panelists receiving a dose of Composition A and Composition B.

TABLE 2

|  | Composition A/ Composition C | Composition A/ Composition B |
|---|---|---|
| Overall Scent | 56 | 53 |
| On application (8-10 am) | 58 | 53 |
| Lunchtime (12-1 pm) | 44 B | 30 |
| Afternoon (3-4 pm) | 41 B | 23 |
| Evening (6-7 pm) | 50 B | 28 |
| Overall Rating | 51 B | 39 |

0 = Poor; 25 = Fair; 50 = Good; 75 = Very Good; 100 = Excellent.

Thus as shown in Table 2, microcapsules having a fracture strength from 0.1 MPa to about 25.0 MPa can survive the spraying process and provide a benefit to the user. In this regard, a significant benefit from the microcapsules was observed as little as 4 hours after application and as long as 11 hours after application. These data suggest that microcapsules with a fracture strength of from 0.1 MPa to about 25.0 MPa are resilient enough to survive a spraying process and are weak enough to rupture and release the encapsulated fragrance during routine usage.

As shown in Table 2B, a dispenser comprising Composition A, a dispenser comprising Composition B, a dispenser comprising Composition C, and a dispenser comprising Composition D were evaluated for their ability to deliver a consumer noticeable fragrance benefit as described below under Consumer Test Protocol I. Composition A included a volatile solvent and a fragrance, and is further described below in Example 2. Composition B included water, and is further described below in Example 2. Composition C included water, a suspending agent, and microcapsules encapsulating a fragrance, and is further described below in Example 2. Composition D included water, a suspending agent, and microcapsules encapsulating a fragrance, and is further described below in Example 2.

Initially, the noticeability upon application of all three Groups was about the same. As shown in Table 2B, after 4-5 hours from application (i.e. 12-1 pm) and 7-8 hours after application (i.e. 3-4 pm), Group III is significantly more noticeable than Groups I or II. After 10-11 hours from application (i.e. 6-7 pm), Group III is significantly more noticeable than Group I. These data suggest that the fracture strength of the particle may influence the noticeability of the encapsulated fragrance. Surprisingly, a low fracture strength of 1.55 MPa is preferred over a high fracture strength of 6.83 MPa, in the earlier part of the day although both the low and high fracture strength microcapsules outperformed the control that did not contain microcapsules. At a later stage in the day, both low and high fracture strength particles are equally preferred over the control that did not contain microcapsules.

TABLE 2B

| | Group I: Composition A & B | Group II: Composition A & C | Group III: Composition A & D |
|---|---|---|---|
| Microcapsules' Fracture Strength | NA | 6.83 MPa | 1.55 MPa |
| Overall experience | 31 | 45 | 59** |
| Overall noticeability | 25 | 34 | 50* |
| Noticeability on application (8-9 am) | 94 | 94 | 93 |
| Noticeability at 12-1 pm | 43 | 52 | 68** |
| Noticeability at 3-4 pm | 23 | 42* | 58** |
| Noticeability at 6-7 pm | 18 | 33* | 36* |

*denotes significance as compared to Group I

**denotes significance as compared to Group I & II

It has also surprisingly been observed that microcapsules having a median volume-weighted particle size of from 10 microns to 20 microns may deliver improved noticeability over microcapsules of other sizes when said microcapsules are sprayed.

Compositions

Volatile Solvents

The compositions described herein may include a volatile solvent or a mixture of volatile solvents. The volatile solvents may comprise greater than 10%, greater than 30%, greater than 40%, greater than 50%, greater than 60%, greater than 70%, or greater than 90%, by weight of the composition. The volatile solvents useful herein may be relatively odorless and safe for use on human skin. Suitable volatile solvents may include $C_1$-$C_4$ alcohols and mixtures thereof. Some non-limiting examples of volatile solvents include ethanol, methanol, propanol, isopropanol, butanol, and mixtures thereof. In some examples, the composition may comprise from 0.01% to 98%, by weight of the composition, of ethanol.

Nonvolatile Solvents

The composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof.

Fragrances

The composition may comprise a fragrance. As used herein, "fragrance" is used to indicate any odoriferous material or a combination of ingredients including at least one odoriferous material. Any fragrance that is cosmetically acceptable may be used in the composition. For example, the fragrance may be one that is a liquid or solid at room temperature. Generally, the non-encapsulated fragrance(s) may be present at a level from about 0.001% to about 40%, from about 0.1% to about 25%, from about 0.25% to about 20%, or from about 0.5% to about 15%, by weight of the composition. Some fragrances can be considered to be volatiles and other fragrances can be considered to be or non-volatiles, as described and defined herein.

A wide variety of chemicals are known as fragrances, non-limiting examples of which include alcohols, aldehydes, ketones, ethers, Schiff bases, nitriles, and esters. More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of about 500° C. or lower, about 400° C. or lower, or about 350° C. or lower. The BP of many fragrances are disclosed in *Perfume and Flavor Chemicals* (Aroma Chemicals), Steffen Arctander (1969). The ClogP value of the individual fragrance materials may be about −0.5 or greater. As used herein, "ClogP" means the logarithm to the base 10 of the octanol/water partition coefficient. The ClogP can be readily calculated from a program called "CLOGP" which is available from Daylight Chemical Information Systems Inc., Irvine Calif., USA or calculated using Advanced Chemistry Development (ACD/Labs) Software V11.02 (© 1994-2014 ACD/Labs). Octanol/water partition coefficients are described in more detail in U.S. Pat. No. 5,578,563.

Examples of suitable aldehyde include but are not limited to: alpha-Amylcinnamaldehyde, Anisic Aldehyde, Decyl Aldehyde, Lauric aldehyde, Methyl n-Nonyl acetaldehyde, Methyl octyl acetaldehyde, Nonylaldehyde, Benzenecarboxaldehyde, Neral, Geranial, 2, 6 octadiene,1,1 diethoxy-3,7dimethyl-, 4-Isopropylbenzaldehyde, 2,4-Dimethyl-3-cyclohexene-1-carboxaldehyde, alpha-Methyl-p-isopropyldihydrocinnamaldehyde, 3-(3-isopropylphenyl) butanal, alpha-Hexylcinnamaldehyde, 7-Hydroxy-3,7-dimethyloctan-1-al, 2,4-Dimethyl-3-Cyclohexene-1-carboxaldehyde, Octyl Aldehyde, Phenylacetaldehyde, 2,4-Dimethyl-3-Cyclohexene-1-carboxaldehyde, Hexanal, 3,7-Dimethyloctanal, 6,6-Dimethylbicyclo[3.1.1]hept-2-ene-2-butanal, Nonanal, Octanal, 2-Nonenal Undecenal, 2-Methyl-4-(2,6,6-trimethyl-1-cyclohexenyl-1)-2-butenal, 2,6-Dimethyloctanal3-(p-Isopropylphenyl)propionaldehyde, 3-Phenyl-4-pentenal Citronellal, o/p-Ethyl-alpha,alpha-, 9-Decenal, dimethyldihydrocinnamaldehyde, p-Isobutyl-alpha-methyldihydrocinnamaldehyde, cis-4-Decen-1-al, 2,5-Dimethyl-2-ethenyl-4-hexenal, trans-2-Methyl-2-butenal, 3-Methylnonanal, alpha-Sinensal, 3-Phenylbutanal, 2,2-Dimethyl-3-phenylpropionaldehyde, m-tert.Butyl-alpha-methyldihydrocinnamic aldehyde, Geranyl oxyacetaldehyde, trans-4-Decen-1-al, Methoxycitronellal, and mixtures thereof.

Examples of suitable esters include but are not limited to: Allyl cyclohexanepropionate, Allyl heptanoate, Allyl Amyl Glycolate, Allyl caproate, Amyl acetate (n-Pentyl acetate), Amyl Propionate, Benzyl acetate, Benzyl propionate, Benzyl salicylate, cis-3-Hexenylacetate, Citronellyl acetate, Citronellyl propionate, Cyclohexyl salicylate, Dihydro Isojasmonate Dimethyl benzyl carbinyl acetate, Ethyl acetate, Ethyl acetoacetate, Ethyl Butyrate, Ethyl-2-methyl butryrate, Ethyl-2-methyl pentanoate Fenchyl acetate (1,3, 3-Trimethyl-2-norbornanyl acetate), Tricyclodecenyl acetate, Tricyclodecenyl propionate, Geranyl acetate, cis-3-Hexenyl isobutyrate, Hexyl acetate, cis-3-Hexenyl salicylate, n-Hexyl salicylate, Isobornyl acetate, Linalyl acetate, p-t-Butyl Cyclohexyl acetate, (−)-L-Menthyl acetate, o-t-Butylcyclohexyl acetate), Methyl benzoate, Methyl dihydro iso jasmonate, alpha-Methylbenzyl acetate, Methyl salicylate, 2-Phenylethyl acetate, Prenyl acetate, Cedryl acetate, Cyclabute, Phenethyl phenylacetate, Terpinyl formate, Citronellyl anthranilate, Ethyl tricyclo[5.2.1.0-2,6]decane-2-carboxylate, n-Hexyl ethyl acetoacetate, 2-tert.-Butyl-4-methyl-cyclohexyl acetate, Formic acid, 3,5,5-trimethylhexyl ester, Phenethyl crotonate, Cyclogeranyl acetate, Geranyl crotonate, Ethyl geranate, Geranyl isobutyrate, Ethyl 2-nonynoate2,6-Octadienoic acid, 3,7-dimethyl-, methyl ester, Citronellyl valerate, 2-Hexenylcyclopentanone, Cyclohexyl anthranilate, L-Citronellyl tiglate, Butyl tiglate, Pentyl tiglate, Geranyl caprylate, 9-Decenyl acetate,2-Isopropyl-5-methylhexyl-1 butyrate, n-Pentyl benzoate, 2-Methylbutyl benzoate (mixture with pentyl benzoate), Dimethyl benzyl carbinyl propionate, Dimethyl benzyl carbinyl acetate, trans-2-Hexenyl salicylate, Dimethyl benzyl carbinyl isobutyrate, 3,7-Dimethyloctyl formate, Rhodinyl formate, Rhodinyl isovalerate, Rhodinyl acetate, Rhodinyl butyrate, Rhodinyl propionate, Cyclohexylethyl acetate, Neryl butyrate, Tetrahydrogeranyl butyrate, Myrcenyl acetate, 2,5-Dimethyl-2-ethenylhex-4-enoic acid, methyl ester, 2,4-Dimethylcyclohexane-1-methyl acetate, Ocimenyl acetate, Linalyl isobutyrate, 6-Methyl-5-heptenyl-1 acetate, 4-Methyl-2-pentyl acetate, n-Pentyl 2-methylbutyrate, Propyl acetate, Isopropenyl acetate, Isopropyl acetate, 1-Methylcyclohex-3-enecarboxylic acid, methyl ester, Propyl tiglate, Propyl/isobutyl cyclopent-3-enyl-1-acetate (alpha-vinyl), Butyl 2-furoate, Ethyl 2-pentenoate, (E)-Methyl 3-pentenoate, 3-Methoxy-3-methylbutyl acetate, n-Pentyl crotonate, n-Pentyl isobutyrate, Propyl formate, Furfuryl butyrate, Methyl angelate, Methyl pivalate, Prenyl caproate, Furfuryl propionate, Diethyl malate, Isopropyl 2-methylbutyrate, Dimethyl malonate, Bornyl formate, Styralyl acetate, 1-(2-Furyl)-1-propanone, 1-Citronellyl acetate, 3,7-Dimethyl-1,6-nonadien-3-yl acetate, Neryl crotonate, Dihydromyrcenyl acetate, Tetrahydromyrcenyl acetate, Lavandulyl acetate, 4-Cyclooctenyl isobutyrate, Cyclopentyl isobutyrate, 3-Methyl-3-butenyl acetate, Allyl acetate, Geranyl formate, cis-3-Hexenyl caproate, and mixtures thereof.

Examples of suitable alcohols include but are not limited to: Benzyl alcohol, beta-gamma-Hexenol (2-Hexen-1-ol), Cedrol, Citronellol, Cinnamic alcohol, p-Cresol, Cumic alcohol, Dihydromyrcenol, 3,7-Dimethyl- 1-octanol, Dimethyl benzyl carbinol, Eucalyptol, Eugenol, Fenchyl alcohol, Geraniol, Hydratopic alcohol, Isononyl alcohol (3,5,5-Trimethyl-1-hexanol), Linalool, Methyl Chavicol (Estragole), Methyl Eugenol (Eugenyl methyl ether), Nerol, 2-Octanol, Patchouli alcohol, Phenyl Hexanol (3-Methyl-5-phenyl-1- pentanol), Phenethyl alcohol, alpha-Terpineol, Tetrahydrolinalool, Tetrahydromyrcenol, 4-methyl-3decen-5-ol, 1-3,7-Dimethyloctane-1-ol, 2-(Furfuryl-2)-heptanol, 6,8-Dimethyl-2-nonanol, Ethyl norbornyl cyclohexanol, beta-Methyl cyclohexane ethanol, 3,7-Dimethyl-(2),6-octen (adien)-1-ol, trans-2-Undecen-1-ol 2-Ethyl-2-prenyl-3-hexenol, Isobutyl benzyl carbinol, Dimethyl benzyl carbinol, Ocimenol, 3,7-Dimethyl-1,6-nonadien-3-ol (cis & trans), Tetrahydromyrcenol, alpha-Terpineol, 9-Decenol-1, 2 (Hexenyl)cyclopentanol, 2,6-Dimethyl-2-heptanol, 3-Methyl-1-octen-3-ol, 2,6-Dimethyl-5-hepten-2-ol, 3,7,9-Trimethyl-1,6-decadien-3-ol, 3,7-Dimethyl-6-nonen-1-ol, 3,7-Dimethyl-1-octyn-3-ol, 2,6-Dimethyl- 1,5,7-octatrienol-3, Dihydromyrcenol, 2,6,10-Trimethyl-5,9-undecadienol, 2,5-Dimethyl-2-propylhex-4-enol-1,(Z),3-Hexenol, o,m,p-Methyl-phenylethanol, 2-Methyl-5-phenyl-1-pentanol, 3-Methylphenethyl alcohol, para-Methyl dimethyl benzyl carbinol, Methyl benzyl carbinol, p-Methylphenylethanol, 3,7-Dimethyl-2-octen-1-ol, 2-Methyl-6-methylene-7-octen-4-ol, and mixtures thereof.

Examples of ketones include but are not limited to: Oxacycloheptadec-10-en-2-one, Benzylacetone, Benzophenone, L-Carvone, cis-Jasmone, 4-(2,6,6-Trimethyl-3-cyclohexen-1-yl)-but-3-en-4-one, Ethyl amyl ketone, alpha-Ionone, Ionone Beta, Ethanone, Octahydro-2,3,8,8-tetramethyl-2-acetonaphthalene, alpha-Irone, 1-(5,5-Dimethyl-1-cyclohexen-1-yl)-4-penten-1-one, 3-Nonanone, Ethyl hexyl ketone, Menthone, 4-Methylacetophenone, gamma-Methyl Ionone Methyl pentyl ketone, Methyl Heptenone (6-Methyl-5-hepten-2-one), Methyl Heptyl ketone, Methyl Hexyl ketone, delta Muscenone, 2-Octanone, 2-Pentyl-3-methyl-2-cyclopenten-1-one, 2-Heptylcyclopentanone, alpha-Methylionone, 3-Methyl-2-(trans-2-pentenyl)-cyclopentenone, Octenyl cyclopentanone, n-Amylcyclopentenone, 6-Hydroxy-3,7-dimethyloctanoic acid lactone, 2-Hydroxy-2-cyclohexen-1-one, 3-Methyl-4-phenyl-3-buten-2-one, 2-Pentyl-2,5,5-trimethylcyclopentanone, 2-Cyclopentylcyclopentanol-1, 5-Methylhexan-2-one, gamma-Dodecalactone, delta-Dodecalactone delta-Dodecalactone, gamma-Nonalactone, delta-Nonalactone, gamma-Octalactone, delta-Undecalactone, gamma-Undecalactone, and mixtures thereof.

Examples of ethers include but are not limited to: p-Cresyl methyl ether, 4,6,6,7,8,8-Hexamethyl-1,3,4,6,7,8-hexahydro-cyclopenta(G)-2-benzopyran, beta-Naphthyl methyl ether, Methyl Iso Butenyl Tetrahydro Pyran, (Phantolide) 5-Acetyl-1,1,2,3,3,6 hexamethylindan, (Tonalid) 7-Acetyl-1,1,3,4,4,6-hexamethyltetralin, 2-Phenylethyl 3-methylbut-2-enyl ether, Ethyl geranyl ether, Phenylethyl isopropyl ether, and mixtures thereof.

Examples of alkenes include but are not limited to: Allo-Ocimene, Camphene, beta-Caryophyllene, Cadinene, Diphenylmethane, d-Limonene, Lymolene, beta-Myrcene, Para-Cymene, alpha-Pinene, beta-Pinene, alpha-Terpinene, gamma-Terpinene, Terpineolene, 7-Methyl-3-methylene-1, 6-octadiene, and mixtures thereof.

Examples of nitriles include but are not limited to: 3,7-Dimethyl-6-octenenitrile, 3,7-Dimethyl-2(3), 6-nonadienenitrile, (2E, 6Z) 2,6-nonadienenitrile, n-dodecane nitrile, and mixtures thereof.

Examples of Schiffs Bases include but are not limited to: Citronellyl nitrile, Nonanal/methyl anthranilate, Anthranilic acid, N-octylidene-, methyl ester(L)-, Hydroxycitronellal/methyl anthranilate, 2-Methyl-3-(4- Cyclamen aldehyde/methyl anthranilate, methoxyphenyl propanal/Methyl anthranilate, Ethyl p-aminobenzoate/hydroxycitronellal, Citral/methyl anthranilate, 2,4-Dimethylcyclohex-3-enecarbaldehyde methyl anthranilate, Hydroxycitronellal-indole, and mixtures thereof.

Non-limiting examples of fragrances include fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract, and mixtures thereof.

Carriers

When the composition contains microcapsules, the composition may include a carrier for the microcapsules. Non-limiting examples of carriers include water, silicone oils like silicone D5, and other oils like mineral oil, isopropyl myristate, and fragrance oils.

The compositions containing microcapsules may include about 0.1% to about 95%, from about 5% to about 95%, or from 5% to 75%, by weight of the composition, of the carrier. When the composition contains a volatile solvent, the composition may include from about 0.01% to about 40%, from about 0.1% to about 30%, or from about 0.1% to about 20%, by weight of the composition, of water.

In some examples, when a first composition containing a volatile solvent and a second composition containing microcapsules are sprayed, the dose containing the mixture of the first and second compositions may contain about 0.01% to about 75%, from about 1% to about 60%, from about 0.01% to about 60%, or from about 5% to about 50%, by weight of the composition, of water.

Encapsulates

The compositions herein may include microcapsules. The microcapsules may be any kind of microcapsule disclosed herein or known in the art. The microcapsules may have a shell and a core material encapsulated by the shell. The core material of the microcapsules may include one or more fragrances. The shells of the microcapsules may be made from synthetic polymeric materials or naturally-occurring polymers. Synthetic polymers can be derived from petroleum oil, for example. Non-limiting examples of synthetic polymers include nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and mixtures thereof. Non-limiting examples of suitable shell materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates; acrylate monomers polymerized via free radical polymerization, and mixtures thereof. Natural polymers occur in nature and can often be extracted from natural materials. Non-limiting examples of naturally occurring polymers are silk, wool, gelatin, cellulose, proteins, and combinations thereof.

The microcapsules may be friable microcapsules. A friable microcapsule is configured to release its core material when its shell is ruptured. The rupture can be caused by forces applied to the shell during mechanical interactions.

The microcapsules may have a median volume weighted fracture strength of from about 0.1 MPa to about 25.0 MPa, when measured according to the Fracture Strength Test Method, or any incremental value expressed in 0.1 mega Pascals in this range, or any range formed by any of these values for fracture strength. As an example, the microcapsules may have a median volume weighted fracture strength of 0.5-25.0 mega Pascals (MPa), alternatively from 0.5-20.0 mega Pascals (MPa), 0.5-15.0 mega Pascals (MPa), 0.5-10.0 mega Pascals (MPa), or alternatively from 1.0-8.0 mega Pascals (MPa).

The microcapsules may have a median volume-weighted particle size of from 2 microns to 80 microns, from 10 microns to 30 microns, or from 10 microns to 20 microns, as determined by the Test Method for Determining Median Volume-Weighted Particle Size of Microcapsules described herein.

The microcapsules may have various core material to shell weight ratios. The microcapsules may have a core material to shell ratio that is greater than or equal to: 10% to 90%, 30% to 70%, 50% to 50%, 60% to 40%, 70% to 30%, 75% to 25%, 80% to 20%, 85% to 15%, 90% to 10%, 95% to 5%, 98% to 2%.

The microcapsules may have shells made from any material in any shape and configuration known in the art. Some or all of the shells may include a polyacrylate material, such as a polyacrylate random copolymer. For example, the polyacrylate random copolymer can have a total polyacrylate mass, which includes ingredients selected from the group including: amine content of 0.2-2.0% of total polyacrylate mass; carboxylic acid of 0.6-6.0% of total polyacrylate mass; and a combination of amine content of 0.1-1.0% and carboxylic acid of 0.3-3.0% of total polyacrylate mass.

When a microcapsule's shell includes a polyacrylate material, the polyacrylate material may form 5-100% of the overall mass, or any integer value for percentage in this range, or any range formed by any of these values for percentage, of the shell. As examples, the polyacrylate material may form at least 5%, at least 10%, at least 25%, at least 33%, at least 50%, at least 70%, or at least 90% of the overall mass of the shell.

The microcapsules may have various shell thicknesses. The microcapsules may have a shell with an overall thickness of 1-2000 nanometers, or any integer value for nanometers in this range, or any range formed by any of these values for thickness. As a non-limiting example, the microcapsules may have a shell with an overall thickness of 2-1100 nanometers.

The microcapsules may also encapsulate one or more benefit agents. The benefit agent(s) include, but are not limited to, one or more of chromogens, dyes, cooling sensates, warming sensates, fragrances, oils, pigments, in any combination. When the benefit agent includes a fragrance, said fragrance may comprise from about 2% to about 80%, from about 20% to about 70%, from about 30% to about 60% of a perfume raw material with a ClogP greater than −0.5, or even from about 0.5 to about 4.5. In some examples, the fragrance encapsulated may have a ClogP of less than 4.5, less than 4, or less than 3. In some examples, the microcapsule may be anionic, cationic, zwitterionic, or have a neutral charge. The benefit agents(s) can be in the form of solids and/or liquids. The benefit agent(s) include any kind of fragrance(s) known in the art, in any combination.

The microcapsules may encapsulate an oil soluble material in addition to the benefit agent. Non-limiting examples of the oil soluble material include mono, di- and tri-esters of $C_4$-$C_{24}$ fatty acids and glycerine; isopropryl myristate, soybean oil, hexadecanoic acid, methyl ester, isododecane, and combinations thereof, in addition to the encapsulated benefit agent. The oil soluble material may have a ClogP about 4 or greater, at least 4.5 or greater, at least 5 or greater, at least 7 or greater, or at least 11 or greater.

The microcapsule's shell may comprise a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is an aminoalkyl acrylate or aminoalkyl methacrylate.

The microcapsules may include a core material and a shell surrounding the core material, wherein the shell comprises: a plurality of amine monomers selected from the group consisting of aminoalkyl acrylates, alkyl aminoalkyl acrylates, dialkyl aminoalykl acrylates, aminoalkyl methacrylates, alkylamino aminoalkyl methacrylates, dialkyl aminoalykl methacrylates, tertiarybutyl aminethyl methacrylates, diethylaminoethyl methacrylates, dimethylaminoethyl methacrylates, dipropylaminoethyl methacrylates, and mixtures thereof; and a plurality of multifunctional monomers or multifunctional oligomers.

Non-limiting examples of microcapsules include microcapsules that comprise a shell comprising an amine selected from the group consisting of diethylaminoethyl methacrylate, dimethylaminoethyl methacrylate, tertiarybutyl aminoethyl methacrylate; and combinations thereof; a core material encapsulated by said shell, said core material comprising about 10% to about 60% of a material selected from the group consisting of mono, di- and tri-esters of $C_4$-$C_{24}$ fatty acids and glycerine; isopropryl myristate, soybean oil, hexadecanoic acid, methyl ester, isododecane, and combinations thereof, by weight of the microcapsule; and about 10% to about 90% of a perfume material, by weight of the microcapsule; wherein said microcapsules have a volume weighted fracture strength from 0.1 MPa to 25 MPa, preferably from 0.8 MPa to 20 MPa, more preferably from 1.0 MPa to 15 MPa; wherein said microcapsules have a median volume-weighted particle size from 10 microns to 30 microns.

Processes for making microcapsules are well known. Various processes for microencapsulation, and exemplary methods and materials, are set forth in U.S. Pat. Nos. 6,592,990; 2,730,456; 2,800,457; 2,800,458; 4,552,811; and U.S. 2006/0263518 A1.

The microcapsule may be spray-dried to form spray-dried microcapsules. The composition may also contain one or more additional delivery systems for providing one or more benefit agents, in addition to the microcapsules. The additional delivery system(s) may differ in kind from the microcapsules. For example, wherein the microcapsule are friable and encapsulate a fragrance, the additional delivery system may be an additional fragrance delivery system, such as a moisture-triggered fragrance delivery system. Non-limiting examples of moisture-triggered fragrance delivery systems include cyclic oligosaccharide, starch (or other polysaccharide material), starch derivatives, and combinations thereof.

The compositions may also include a parent fragrance and one or more encapsulated fragrances that may or may not differ from the parent fragrance. For example, the composition may include a parent fragrance and a non-parent fragrance. A parent fragrance refers to a fragrance that is dispersed throughout the composition and is typically not encapsulated when added to the composition. Herein, a non-parent fragrance refers to a fragrance that differs from a parent fragrance and is encapsulated with an encapsulating material prior to inclusion into a composition. Non-limiting examples of differences between a fragrance and a non-parent fragrance include differences in chemical make-up.

Suspending Agents

The compositions described herein may include one or more suspending agents to suspend the microcapsules and other water-insoluble material dispersed in the composition. The concentration of the suspending agent may range from about 0.01% to about 90%, alternatively from about 0.01% to about 15% by weight of the composition, alternatively from about 0.1% to about 5%.

Non-limiting examples of suspending agents include anionic polymers, cationic polymers, and nonionic polymers. Non-limiting examples of said polymers include vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate and alginic acid, propylene glycol esters, acrylate polymers such as sodium polyacrylate, polyethylacrylate, polyacrylamide, and polyethyleneimine, and inorganic water soluble material such as bentonite, aluminum magnesium silicate, laponite, hectonite, and anhydrous silicic acid. Other suspending agents may include, but are not limited to, Konjac, Gellan, and a methyl vinyl ether/maleic anhydride copolymer crosslinked with decadiene (e.g. Stabileze®).

Other non-limiting examples of suspending agents include cross-linked polyacrylate polymers like Carbomers with the trade names Carbopol® 934, Carbopol® 940, Carbopol® 950, Carbopol® 980, Carbopol® 981, Carbopol® Ultrez 10, Carbopol® Ultrez 20, Carbopol® Ultrez 21, Carbopol® Ultrez 30, Carbopol® ETD2020, Carbopol® ETD2050, Pemulen® TR-1, and Pemulen® TR-2, available from The Lubrizol Corporation; acrylates/steareth-20 methacrylate copolymer with trade name ACRYSOL™ 22 available from Rohm and Hass; acrylates/beheneth-25 methacrylate copolymers, trade names including Aculyn-28 available from Rohm and Hass, and Volarest™ FL available from Croda; nonoxynyl hydroxyethylcellulose with the trade name Amercell™ POLYMER HM-1500 available from Amerchol; methylcellulose with the trade name BENECEL®, hydroxyethyl cellulose with the trade name NATROSOL®; hydroxypropyl cellulose with the trade name KLUCEL®; cetyl hydroxyethyl cellulose with the trade name POLYSURF® 67, supplied by Hercules; ethylene oxide and/or propylene oxide based polymers with the trade names CARBOWAX® PEGs, POLYOX WASRs, and UCON® FLUIDS, all supplied by Amerchol; ammonium acryloyl dimethyltaurate/carboxyethyl-acrylate-crosspolymers like Aristoflex® TAC copolymer, ammonium acryloyl dimethyltaurate/VP copolymers like Aristoflex® AVS copolymer, sodium acryloyl dimethyltaurate/VP crosspolymers like Aristoflex® AVS copolymer, ammonium acryloyl dimethyltaurate/beheneth-25 methacrylate crosspolymers like Aristoflex® BVL or HMB, all available from Clariant Corporation; polyacrylate crosspoylmer-6 with the trade name Sepimax™ Zen, available from Seppic; and cross-linked copolymers of vinyl pyrrolidone and acrylic acid such as UltraThix™ P-100 polymer available from Ashland.

Other non-limiting examples of suspending agents include crystalline suspending agents which can be categorized as acyl derivatives, long chain amine oxides, and mixtures thereof.

Other non-limiting examples of suspending agents include ethylene glycol esters of fatty acids, in some aspects those having from about 16 to about 22 carbon atoms; ethylene glycol stearates, both mono and distearate, in some aspects, the distearate containing less than about 7% of the mono stearate; alkanol amides of fatty acids, having from about 16 to about 22 carbon atoms, or about 16 to 18 carbon atoms, examples of which include stearic monoethanolamide, stearic diethanolamide, stearic monoisopropanolamide and stearic monoethanolamide stearate; long chain acyl derivatives including long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin), a commercial example of which is Thixin® R available from Rheox, Inc. Other non-limiting examples of suspending agents include long chain acyl derivatives, ethylene glycol esters of long chain carboxylic acids, long chain amine oxides, and alkanol amides of long chain carboxylic acids.

Other non-limiting examples of suspending agents include long chain acyl derivatives including N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Non-limiting examples of suitable long chain amine oxides for use as suspending agents include alkyl dimethyl amine oxides (e.g., stearyl dimethyl amine oxide).

Other non-limiting suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Other non-limiting examples of suspending agents include di(hydrogenated tallow) phthalic acid amide, and cross-linked maleic anhydride-methyl vinyl ether copolymer.

Preservatives

Where the composition is aqueous, the compositions herein may include a preservative to prevent growth of unwanted micro-organisms. However, where microcapsules are in the aqueous phase, selection of the preservative can be tricky as not all preservatives are compatible with the microcapsules. Suitable preservatives which may be used with polyacrylates microcapsules may include but are not limited to: parahydroxybenzoates or esters of parahydroxybenzoic acids and their salts, phenoxyethanol, benzoic acid, sodium benzoate, salicylic acid, sorbic acid and its salts, dehydroacetic acid, DMDM Hydantoin, and combinations thereof.

Coloring Agents

The compositions herein may include a coloring agent. A coloring agent may be in the form of a pigment. As used herein, the term "pigment" means a solid that reflects light of certain wavelengths while absorbing light of other wavelengths, without providing appreciable luminescence. Useful pigments include, but are not limited to, those which are extended onto inert mineral(s) (e.g., talk, calcium carbonate, clay) or treated with silicone or other coatings (e.g., to prevent pigment particles from re-agglomerating or to change the polarity (hydrophobicity) of the pigment. Pigments may be used to impart opacity and color. Any pigment that is generally recognized as safe (such as those listed in C.T.F.A. cosmetic Ingredient Handbook, $3^{rd}$ Ed., cosmetic and Fragrance Association, Inc., Washington, D.C. (1982), herein incorporated by reference) may be included in the compositions described herein. Non-limiting examples of pigments include body pigment, inorganic white pigment, inorganic colored pigment, pearling agent, and the like. Non-limiting examples of pigments include talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like. The aforementioned pigments can be used independently or in combination.

Other non-limiting examples of pigments include inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Non-limiting examples of pigments include nanocolorants from BASF and multi-layer interference pigments such as Sicopearls from BASF. The pigments may be surface treated to provide added stability of color and ease of formulation. Non-limiting examples of pigments include aluminum, barium or calcium salts or lakes. Some other non-limiting examples of coloring agents include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

A coloring agent may also be a dye. Non-limiting examples include Red 6, Red 21, Brown, Russet and Sienna dyes, Yellow 5, Yellow 6, Red 33, Red 4, Blue 1, Violet 2, and mixtures thereof. Other non-limiting examples of dyes include fluorescent dyes like fluorescein.

Modulators & Co-Modulators

The first composition, when containing a volatile solvent, may also comprise at least one non-odorous modulator formed from an alkoxylated glucoside, like methyl glucoside polyol, ethyl glucoside polyol, and propyl glucoside polyol. The modulator can be a compound of formula (I):

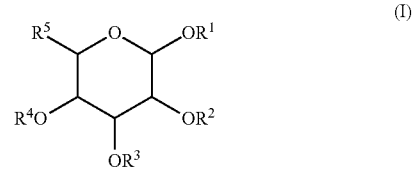

wherein:

$R^1$ is hydrogen, alkyl, alkenyl or alkynyl;

$R^2$ is selected from hydrogen, alkyl, alkenyl, alkynyl, —[$R^6R^7(R^8)O]_wR^9$, wherein w is from 1 to 10, or 2 to 9;

$R^3$ is selected from hydrogen, alkyl, alkenyl, alkynyl, —[$R^6R^7(R^8)O]_yR^9$, wherein y is from 1 to 10, or 2 to 9;

$R^4$ is selected from hydrogen, alkyl, alkenyl, alkynyl, —[$R^6R^7(R^8)O]_xR^9$, wherein x is from 1 to 10, or 2 to 9;

$R^5$ is selected from hydrogen, alkyl, alkenyl, alkynyl, —$R^6OR^9$, —$R^6O[R^6R^7(R^8)O]_zR^9$, wherein z is from 1 to 10, or 2 to 9;

each $R^6$ and $R^7$ are independently selected from alkylene, alkenylene, or alkynylene; and each $R^8$ and $R^9$ is independently selected from hydrogen or alkyl, The sum of w, y, x and z can be, for example, equal to 4 to 40, 8 to 36, 10 to 32, 10 to 28, or combinations thereof.

One exemplary modulator is Undecyl Glucoside and is available under the tradename Simulsol® SL 11 W from SEPPIC, France.

A modulator may also be a compound of formula (Ia):

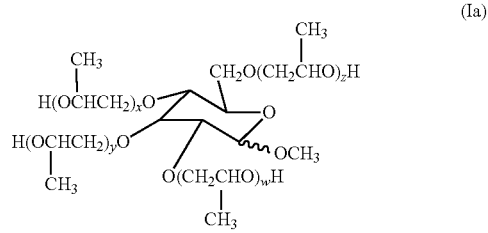

The sum of w+x+y+z is, for example, equal to 4 to 40, 8 to 36, 10 to 32, 10 to 28, or combinations thereof. Exemplary modulators of Formula Ia can include a PPG-10 Methyl Glucose Ether available under the tradename Glucam™ P-10 or Ethoxylated Methyl Glucose Ether and is available under the tradename Glucam™ E-20, respectively, from Lubrizol (USA), or a PPG-20 Methyl Glucose Ether, available under the tradename Glucam™ P-20 from Lubrizol (USA).

A modulator can have a compound of formula (II):

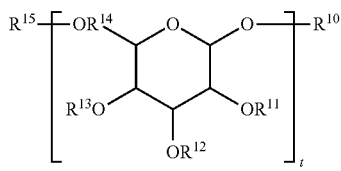

wherein:

$R^{10}$ is hydrogen, alkyl, alkenyl, or alkynyl;

each $R^{11}$ is independently selected from hydrogen, alkyl, alkenyl, alkynyl;

each $R^{12}$ is independently selected from hydrogen, alkyl, alkenyl, or alkynyl;

each $R^{13}$ is independently selected from hydrogen, alkyl, alkenyl, or alkynyl;

each $R^{14}$ is selected from alkylene, alkenylene, or alkynylene; and $R^{15}$ is hydrogen, alkyl, alkenyl, or alkynyl;

wherein t is 5 or less, like 1, 2, or 3.

An exemplary modulator of formula (II) is Caprylyl/Capryl Glucoside and is available under the tradename Plantacare® 810 UP from BASF, Ludwigshafen, Germany.

In another aspect, the first composition further comprises one or more non-odorous fragrance co-modulators, selected from the group consisting of: Isocetyl alcohol (CERAPHYL® ICA); PPG-3 myristyl ether (like Tegosoft™ APM and/or Varonic® APM); Neopentyl glycol diethylhexanoate (like Schercemol™ NGDO); and mixtures thereof. PPG-3 myristyl ether is commercialized by various suppliers including: Evonik-Goldschmidt under the tradename Tegosoft™ APM; Degussa under the tradename Varonic® APM; International Speciality Products as a mixture of PPG-3 myristyl ether with isocetyl alcohol; Lubrizol Advanced Materials (USA) as a mixture of PPG-3 myristyl ether with neopentyl glycol diethylhexanoate under the tradename Schercemol™ NGDO ester; and combinations thereof. Such commercial forms of PPG-3 myristyl ether and mixtures thereof, are appropriate for use as co-modulators in the first composition.

In one example, least 50 wt % of the non-odorous fragrance modulator is PPG-20 Methyl Glucose Ether, with the remainder to 100 wt % possibly being one or more other modulators or co-modulators.

In yet another aspect, the first composition comprises one or more non-odorous fragrance co-modulators selected from the group consisting of: Isocetyl alcohol (CERAPHYL® ICA); PPG-3 myristyl ether (preferably Tegosoft™ APM and/or Varonic® APM); Neopentyl glycol diethylhexanoate (preferably Schercemol™ NGDO); and mixtures thereof. Going further, the composition can be substantailly free of or free of non-odorous modulators formed from an alkoxylated glucoside selected from the group consisting of methyl glucoside polyol, ethyl glucoside polyol and propyl glucoside polyol.

Other Ingredients

The compositions may include other ingredients like antioxidants, ultraviolet inhibitors like sunscreen agents and physical sunblocks, cyclodextrins, quenchers, and/or skin care actives. Non-limiting examples of other ingredients include 2-ethylhexyl-p-methoxycinnamate; hexyl 2-[4-(di-ethylamino)-2-hydroxybenzoyl]benzoate; 4-tert-butyl-4'-methoxy dibenzoylmethane; 2-hydroxy-4-methoxybenzophenone; 2-phenylbenzimidazole-5-sulfonic acid; octocrylene; zinc oxide; titanium dioxide; vitamins like vitamin C, vitamin B, vitamin A, vitamin E, and derivatives thereof; flavones and flavonoids; amino acids like glycine, tyrosine, etc.; carotenoids and carotenes; chelating agents like EDTA, lactates, citrates, and derivatives thereof.

Dispenser

In some examples, the dispenser may include at least one dispensing end and at least two reservoirs. The dispenser may be such a size as to allow being handheld. The dispenser may also include at least two pumps, one for each reservoir. The dispenser may include a system for atomizing the first and second compositions for spraying the compositions such as by including a swirl chamber. The dispenser containing the at least two reservoirs may be configured to either mix the two compositions prior to exiting the dispenser or mix the two compositions in-flight (i.e. upon exit of the dispenser). Non-limiting examples of dispensers are described in EP0775530B1, EP1633490, and below.

The dispenser may include a first composition stored in a first reservoir and a second composition stored in the second reservoir. The first composition may include a volatile solvent and a first fragrance. The second composition may include a plurality of microcapsules and a carrier (e.g. water). The second composition my further include a suspending agent. The first and second compositions may each further include any other ingredient listed herein unless such an ingredient negatively affects the performance of the microcapsules. Non-limiting examples of other ingredients include a coloring agent included in at least one of the first and second compositions and at least one non-encapsulated fragrance in the first composition. When the second composition comprises microcapsules encapsulating a fragrance, the second compositions may further include a non-encapsulated fragrance that may or may not differ from the encapsulated fragrance in chemical make-up. In some examples, the second composition may be substantially free of a material selected from the group consisting of a propellant, ethanol, a detersive surfactant, and combinations thereof; preferably free of a material selected from the group consisting of a propellant, ethanol, a detersive surfactant, and combinations thereof. Non-limiting examples of propellants include compressed air, nitrogen, inert gases, carbon dioxide, gaseous hydrocarbons like propane, n-butane, isobutene, cyclopropane, and mixtures thereof. In some examples, the first composition may be substantially free of a material selected from the group consisting of a propellant, microcapsules, a detersive surfactant, and combinations thereof; preferably free of a material selected from the group consisting of propellant, microcapsules, a detersive surfactant, and combinations thereof.

The dispenser may be designed to dispense a volume ratio of the first composition to the second composition at a ratio from 10:1 to 1:10, from 5:1 to 1:5, from 3:1 to 1:3, from 2:1 to 1:2, or even 1:1 to 2:1, when the first composition comprises a volatile solvent and the second composition comprises a carrier and a plurality of microcapsules. The dispenser may dispense a first dose of the first composition and a second dose of the second composition such that the first dose and the second dose have a combined volume of from 30 microliters to 300 microliters, alternatively from 50 microliters to 140 microliters, alternatively from 70 microliters to 130 microliters. At least some of the microcapsules included in such a dispenser may encapsulate a fragrance. The fragrance encapsulated within the microcapsules may or may not differ in chemical make-up from the non-encapsulated fragrance included with the volatile solvent.

As shown in FIG. 1 and FIG. 2, the dispenser 10 may have a housing 20, an actuator 30 and an exit orifice 40. In some non-limiting examples, the exit orifice may have a volume of 0.01 cubic millimeters to 0.20 cubic millimeters, such as when the exit orifice 40 has a volume of 0.03 cubic millimeters. In some examples, the housing 20 may not be necessary; a non-limiting example of which is when the reservoirs 50, 60 are glass bottles (not shown). When the reservoirs are made of glass, the two reservoirs may be blown from the same piece of molten glass, appearing as a single bottle with two reservoirs. Alternatively, when the reservoirs are made of glass, the two reservoirs may be blown from separate pieces of molten glass, appearing as two bottles, each with a single reservoir, and joined together via a connector. One of ordinary skill in the art will appreciate that many possible designs of the reservoirs are possible without deviating from the teachings herein; a non-limiting example of which is a reservoir within a reservoir.

As shown in FIG. 3, the dispenser 10 may also contain a first reservoir 50 for storing a first composition 61 and a second reservoir 60 for storing a second composition 51. The reservoirs 50, 60 may be of any shape or design. The dispenser may be configured to dispense a similar volume ratio (e.g. 1:1) of the first composition 51 to the second composition 61 as shown in FIG. 3. The first reservoir 50 may have an open end 52 and a closed end 53. The second reservoir may have an open end 62 and a closed end 63. The open ends 52, 62 may be used, for example, to insert the pumps, and/or dip tubes into the reservoirs. The open ends 52, 62 may also be used to supply the reservoirs with the compositions. Once supplied, the open ends 52, 62 may be capped or otherwise sealed to prevent leakage from the reservoirs. In some examples, the second composition 61 may include microcapsules 55. The dispenser may include a first dip tube 70 and a second dip tube 80, although the dip tubes are not necessary if alternative means are provided for airless communication between the reservoir and the pump, a non-limiting example of which is a delaminating bottle. The dispenser may include a first pump 90 (shown as a schematic) in communication with the first dip tube 70. The dispenser may also include a second pump 100 (shown as a schematic) in communication with the second dip tube 80. The inner workings of the pumps are routine unless otherwise illustrated in the drawings. Such inner workings have been abbreviated and shown as schematic so as to not detract from the inventions herein. Suitable pumps with outputs between 30 microliters to 140 microliter may be obtained from suppliers such as Aptargroup Inc., MeadWeastavo Corp., and Albea. Some examples of suitable pumps are the pre-compression pumps described in WO2012110744, EP0757592, EP0623060. The first pump 90 may have a chamber 91 and the second pump 100 may have a chamber 101.

The dispenser may include a first channel 110 and a second channel 120. In some non-limiting examples, the channels 110, 120 have a volume of 5 millimeters to 15 millimeters, an example of which is when the channels have a volume of 8.4 cubic millimeters. The first channel 110 may have a proximal end 111 and a distal end 112. The second channel 120 may have a proximal end 121 and a distal end 122. The proximal end 111 of the first channel 110 is in communication with the exit tube 92 of the first pump 90. The proximal end 121 of the second channel 120 is in communication with the exit tube 102 of the second pump 100. The first channel 110 may be of a shorter length as compared to the second channel 120. The second channel 120 may be disposed above the first channel 110 as illustrated in FIG. 3 or below the first channel 110. Alternatively, the first channel and second channel may be substantially coplanar (i.e. exist side-by-side). The exit tubes 92, 102 may have similar or different diameters which can provide for similar or different volumes. In some non-limiting examples, the exit tubes have a diameter of 0.05 millimeters to 3 millimeters, an example of which is when one of the exit tubes has a diameter of 1.4 millimeters and the other exit tube has a diameter of 1 millimeter. In some non-limiting examples, the exit tubes 92, 102 may have a volume of from 2 cubic millimeters to 10 cubic millimeters, such as when one exit tube has a volume of 7.70 cubic millimeters and the other exit tube as a volume of 3.93 cubic millimeters.

The distal end 112 of the first channel 110 and the distal end 122 of the second channel 120 serve to deliver the compositions into the swirl chamber 130. The swirl chamber 130 may impart on the first composition 51 and the second composition 61 a swirl motion. The swirl chamber may be configured to deliver certain spray characteristics. For example, the fluid entering the swirl chamber may be provided a swirling or circular motion or other shape of motion within the swirl chamber, the characteristics of the motion being driven by the inward design of the swirl chamber 130. Incorporation of a swirl chamber 130 may provide sufficient atomization when compositions that vary in surface tension and viscosity are present in the reservoirs. In some instances, the mixing of the two compositions in the swirl chamber may lower the surface tension of the compositions, and thereby, improve the level of atomization of the liquids.

Figure 5:
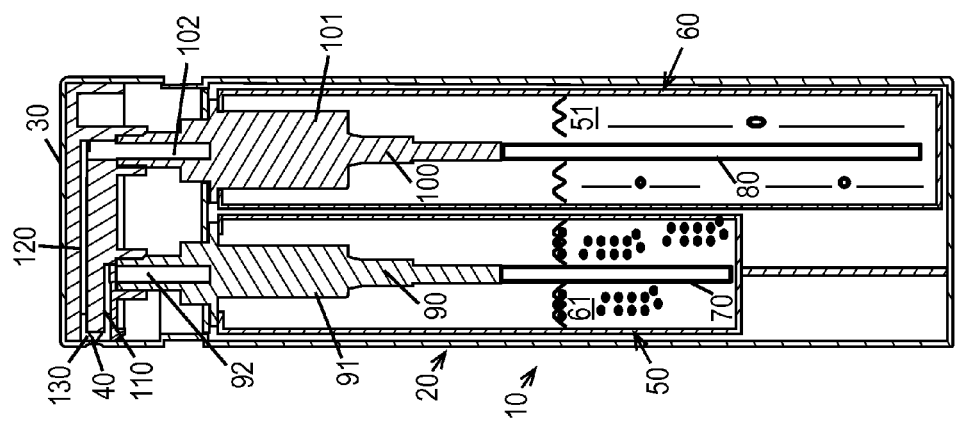
FIG. 5 is a cross sectional view of the side of a dispenser.

The dispenser may also be configured to dispense different ratios of the first composition 51 to the second composition 61. The dispenser may also be configured to contain a first pump and a second pump with different output volumes. In some non-limiting examples, at least one pump may have an output of 70 microliters and the other pump may have an output of 50 microliters. As shown in FIG. 4, the first reservoir 50 may be configured to hold a smaller volume than the second reservoir 150 or vice versa. If dip tubes are included, the first dip tube 70 may also be of a shorter length than the second dip tube 80 or vice versa. Alternatively, the reservoirs 50 and 60 could be the same size, while under filling the first reservoir 50. As shown in FIG. 4, the first pump 90 and the second pump 100 may be configured so that the chambers 91, 101 have different diameters while having the same or similar lengths that allow for the same or similar stroke lengths for the pistons. Alternatively, as illustrated in FIG. 5, the first pump 90 and second pump 100 may be configured so that the chambers 91, 101 have different lengths and similar or the same diameters. Such configurations may deliver in series dispensing of a larger volume of either composition 51, 61 by allowing for pistons of different sizes.

Alternatively, the first and second compositions may be stored in different dispensers and sprayed sequentially or concurrently. In this regard, a first dispenser may be used to store and apply the first composition which comprises a volatile solvent and a first fragrance. A second dispenser may then be used to store and apply the second composition comprising a plurality of microcapsules and a carrier (e.g. water). The second composition my further include a suspending agent. The first and second compositions may each further include any other ingredient listed herein unless such an ingredient negatively affects the performance of the microcapsules. In this regard, a coloring agent may be included in at least one of the first and second compositions.

In some examples, the second composition may be substantially free of a material selected from the group consisting of a propellant, ethanol, a detersive surfactant, and combinations thereof; preferably free of a material selected from the group consisting of a propellant, ethanol, a detersive surfactant, and combinations thereof. In some examples, the first composition may be substantially free of a material selected from the group consisting of a propellant, microcapsules, a detersive surfactant, and combinations thereof; preferably free of a material selected from the group consisting of propellant, microcapsules, a detersive surfactant, and combinations thereof.

Said first and second dispenser may be sold individually or as a kit, with or without written instructions instructing the user to apply the two compositions sequentially and/or concurrently. Non-limiting examples of written instructions include: 1) instructing a user to spray a first composition containing the volatile solvent and first fragrance and a second composition containing the microcapsules sequentially, and optionally, relatively in the same area; 2) instructing a user to spray a first composition containing the volatile solvent and first fragrance and a second composition containing the microcapsules sequentially concurrently, and, optionally, relatively in the same area; and 3) instructing a user to spray a first composition containing the volatile solvent and first fragrance and a second composition containing the microcapsules and doing so while avoiding contact with the eyes and/or face. In some examples, a customer may be provided an assortment of second dispensers that may vary by the design of the dispenser, the type of microcapsule, the type of fragrance encapsulated by the microcapsules, and combinations thereof for which to select for pairing with the first dispenser containing the volatile solvent and first fragrance.

Second Composition

In some examples, the second composition may include at least 50%, at least 75%, or even at least 90%, by weight of the composition, of water; a plurality of microcapsules; and from about 0.01% to about 90%, preferably from about 0.01% to about 15%, more preferably from about 0.1% to about 5%, by weight of the composition, of a suspending agent; wherein the composition is free of propellants, ethanol, and detersive surfactants; wherein the microcapsules comprise a first fragrance and a shell that surrounds said first fragrance. In some examples, the second composition may be substantially free of, or alternatively, free of a wax, an antiperspirant, and combinations thereof. In some examples, the second composition may comprise about 20% or less, about 10% or less, about 7% or less, of the microcapsules. It is to be appreciated that because the second composition is to be atomized, the concentration of the microcapsules in the second composition should not be so high as to prevent suitable atomization.

Method of Use

The compositions disclosed herein may be applied to one or more skin surfaces and/or one or more mammalian keratinous tissue surfaces as part of a user's daily routine or regimen. Additionally or alternatively, the compositions herein may be used on an "as needed" basis. The composition may be applied to any article, such as a textile, or any absorbent article including, but not limited to, feminine hygiene articles, diapers, and adult incontinence articles. For example, the compositions may be used as a body spray, feminine spray, adult incontinence spray, baby spray, fine fragrance spray, or other spray. The size, shape, and aesthetic design of the dispensers described herein may vary widely as may the mechanical design of the dispenser. The compositions may be applied simultaneously or sequentially, depending on the choice of dispenser or dispensers.

Consumer Test Protocol I

Evaluations were conducted under controlled environmental conditions by an untrained panel using the following standardized procedures. 14-24 untrained panelists participated in each evaluation. The panelists were split into two groups: Group A and Group B. Group A were treated with an article containing Composition A and an article containing Composition B for use during week 1. Group B were treated with an article containing Composition A and an article containing Composition C for use during week 1. Group A were treated with an article containing Composition A and an article containing Composition C for use during week 2. Group B were treated with an article containing Composition A and an article containing Composition B for use during week 1. Composition A, Composition B, and Composition C are described below.

Each article included a glass bottle for storing the composition and an Aptar VP4 70 µl pump spray. Each article was sprayed approximately 10 centimeters from the situs. On each application area, one 70 µl dose of Composition A and one 70 µl dose of Composition B/C was sprayed on top of each other. The application areas consisted of two sites on the forearm and two sites on the neck.

At the end of each week, each panelist was provided a questionnaire containing the following questions:

How would you rate the SCENT of the perfume at the following time points? (Please mark one box for each time point.)

|  | Excellent | Very Good | Good | Fair | Poor | Not able to smell any more |
|---|---|---|---|---|---|---|
| Overall Scent | ☐ | ☐ | ☐ | ☐ | ☐ | ☐ |
| . . . just after it was applied on you | ☐ | ☐ | ☐ | ☐ | ☐ | ☐ |
| . . . lunchtime (~12-1 pm) | ☐ | ☐ | ☐ | ☐ | ☐ | ☐ |
| . . . afternoon (~3-4 pm) | ☐ | ☐ | ☐ | ☐ | ☐ | ☐ |
| . . . evening (~6-7 pm) | ☐ | ☐ | ☐ | ☐ | ☐ | ☐ |

Overall Experience

Considering everything about the perfume you have tried today, please indicate which of the following best describes your OVERALL OPINION OF THE PERFUME EXPERIENCE? (Select one response)

| Excellent | Very Good | Good | Fair | Poor |
|---|---|---|---|---|
| ☐ | ☐ | ☐ | ☐ | ☐ |

Noticeability questions were asked as follows:

Please answer the following questions JUST AFTER THE PERFUME WAS APPLIED ON YOU. Please circle your choice

| Which of the following best describes the NOTICEABILITY of the perfume? | I am continuously aware of the perfume | I get frequent wafts of the perfume | I get occasional wafts of the perfume | I have to smell my skin to make myself aware of the perfume | I am not aware of the perfume |
|---|---|---|---|---|---|

For the noticeability questions (Application, lunchtime, afternoon and evening the coding was as follows:
0=I am not aware of the perfume; 25=I have to smell my skin to make myself aware of the perfume; 50=I get occasional wafts of the perfume; 75=I get frequent wafts of the perfume; 100=I am still continuously aware of the perfume The overall experience and overall noticeability was asked on a Poor to excellent scale:
0=Poor; 25=Fair; 50=Good; 75=Very Good; 100=Excellent At the end of week 1 and 2, the evaluations provided by each panelist were recorded. The statistical test used was the Student T-Test (paired samples). The results of the questionnaire are illustrated in Table 2. An average score of 0 indicates that the panelists are no longer aware of the fragrance. A score of 25-49, indicates that the panelists can smell their skin to make themselves aware of the fragrance. A score of 50-74 indicates that the panelists received frequent wafts of the fragrance. A score of 75-100 indicates that the panelists were continuously aware of the fragrance. Referring to Table 2, the confidence interval was 90% and the letter B corresponds to a significant difference over Column B.

Test Methods

It is understood that the test methods that are disclosed in the Test Methods Section of the present application should be used to determine the respective values of the parameters of Applicants' invention as such invention is described and claimed herein.

(1) Fracture Strength Test Method

One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in de-ionized (DI) water to form a slurry for characterization. It is to be understood that the fracture strength of microcapsules extracted from a finished product may vary +/−15% from the ranges described herein as the finished product may alter the microcapsules' fracture strength over time.

To calculate the percentage of microcapsules which fall within a claimed range of fracture strengths, three different measurements are made and two resulting graphs are utilized. The three separate measurements are namely: i) the volume-weighted particle size distribution (PSD) of the microcapsules; ii) the diameter of at least 10 individual microcapsules within each of 3 specified size ranges, and; iii) the rupture-force of those same 30 or more individual microcapsules. The two graphs created are namely: a plot of the volume-weighted particle size distribution data collected at i) above; and a plot of the modeled distribution of the relationship between microcapsule diameter and fracture-strength, derived from the data collected at ii) and iii) above. The modelled relationship plot enables the microcapsules within a claimed strength range to be identified as a specific region under the volume-weighted PSD curve, and then calculated as a percentage of the total area under the curve.

a.) The volume-weighted particle size distribution (PSD) of the microcapsules is determined via single-particle optical sensing (SPOS), also called optical particle counting (OPC), using the AccuSizer 780 AD instrument, or equivalent, and the accompanying software CW788 version 1.82 (Particle Sizing Systems, Santa Barbara, Calif., U.S.A.). The instrument is configured with the following conditions and selections: Flow Rate=1 ml/sec; Lower Size Threshold=0.50 μm; Sensor Model Number=LE400-05SE; Autodilution=On; Collection time=120 sec; Number channels=512; Vessel fluid volume=50 ml; Max coincidence=9200. The measurement is initiated by putting the sensor into a cold state by flushing with water until background counts are less than 100. A sample of microcapsules in suspension is introduced, and its density of particles is adjusted with DI water as necessary via autodilution to result in particle counts of at least 9200 per ml. During a time period of 120 seconds the suspension is analyzed. The resulting volume-weighted PSD data are plotted and recorded, and the values of the mean, $10^{th}$ percentile, and $90^{th}$ percentile are determined.

b.) The diameter and the rupture-force value (also known as the bursting-force value) of individual microcapsules are measured via a computer-controlled micromanipulation instrument system which possesses lenses and cameras able to image the microcapsules, and which possesses a fine, flat-ended probe connected to a force-transducer (such as the Model 403A available from Aurora Scientific Inc, Canada, or equivalent), as described in: Zhang, Z. et al. (1999) "Mechanical strength of single microcapsules determined by a novel micromanipulation technique." *J. Microencapsulation*, vol 16, no. 1, pages 117-124, and in: Sun, G. and Zhang, Z. (2001) "Mechanical Properties of Melamine-Formaldehyde microcapsules." *J. Microencapsulation*, vol 18, no. 5, pages 593-602, and as available at the University of Birmingham, Edgbaston, Birmingham, UK.

c.) A drop of the microcapsule suspension is placed onto a glass microscope slide, and dried under ambient conditions for several minutes to remove the water and achieve a sparse, single layer of solitary particles on the dry slide. Adjust the concentration of microcapsules in the suspension as needed to achieve a suitable particle density on the slide. More than one slide preparation may be needed.

d.) The slide is then placed on a sample-holding stage of the micromanipulation instrument. Thirty or more microcapsules on the slide(s) are selected for measurement, such that there are at least ten microcapsules selected within each of three pre-determined size bands. Each size band refers to the diameter of the microcapsules as derived from the Accusizer-generated volume-weighted PSD. The three size bands of particles are: the Mean Diameter+/−2 μm; the $10^{th}$ Percentile Diameter+/−2 μm; and the $90^{th}$ Percentile Diameter+/−2 μm. Microcapsules which appear deflated, leaking or damaged are excluded from the selection process and are not measured.

e.) For each of the 30 selected microcapsules, the diameter of the microcapsule is measured from the image on the micromanipulator and recorded. That same microcapsule is then compressed between two flat surfaces, namely the flat-ended force probe and the glass microscope slide, at a speed of 2 μm per second, until the microcapsule is ruptured. During the compression step, the probe force is continuously measured and recorded by the data acquisition system of the micromanipulation instrument.

f.) The cross-sectional area is calculated for each of the selected microcapsules, using the diameter measured and assuming a spherical particle ($\pi r^2$, where r is the radius of the particle before compression). The rupture force is determined for each selected particle from the recorded force probe measurements, as demonstrated in Zhang, Z. et al. (1999) "Mechanical strength of single microcapsules determined by a novel micromanipulation technique." *J. Microencapsulation*, vol 16, no. 1, pages 117-124, and in: Sun, G. and Zhang Z. (2001) "Mechanical Properties of Melamine-Formaldehyde microcapsules." J. Microencapsulation, vol 18, no. 5, pages 593-602.

g.) The Fracture Strength of each of the 30 or more microcapsules is calculated by dividing the rupture force (in Newtons) by the calculated cross-sectional area of the respective microcapsule.

h.) On a plot of microcapsule diameter versus fracture-strength, a Power Regression trend-line is fit against all 30 or more raw data points, to create a modeled distribution of the relationship between microcapsule diameter and fracture-strength.

i.) The percentage of microcapsules which have a fracture strength value within a specific strength range is determined by viewing the modeled relationship plot to locate where the curve intersects the relevant fracture-strength limits, then reading off the microcapsule size limits corresponding with those strength limits. These microcapsule size limits are then located on the volume-weighted PSD plot and thus identify an area under the PSD curve which corresponds to the portion of microcapsules falling within the specified strength range.

The identified area under the PSD curve is then calculated as a percentage of the total area under the PSD curve. This percentage indicates the percentage of microcapsules falling with the specified range of fracture strengths.

(2) ClogP

The "calculated log P" (Clog P) is determined by the fragment approach of Hansch and Leo (cf., A. Leo, in Comprehensive Medicinal Chemistry, Vol. 4, C. Hansch, P. G. Sammens, J. B. Taylor, and c. A. Ramsden, Eds. P. 295, Pergamon Press, 1990, incorporated herein by reference). ClogP values may be calculated by using the "CLOGP" program available from Daylight Chemical Information Systems Inc. of Irvine, Calif. U.S.A. or calculated using Advanced Chemistry Development (ACD/Labs) Software V11.02 (© 1994-2014 ACD/Labs).

(3) Boiling Point

Boiling point is measured by ASTM method D2887-04a, "Standard Test Method for Boiling Range Distribution of Petroleum Fractions by Gas Chromatography," ASTM International.

(4) Volume Weight Fractions

Volume weight fractions are determined via the method of single-particle optical sensing (SPOS), also called optical particle counting (OPC). Volume weight fractions are determined via an AccuSizer 780/AD supplied by Particle Sizing Systems of Santa Barbara Calif., U.S.A. or equivalent.

Procedure:

1) Put the sensor in a cold state by flushing water through the sensor.
2) Confirm background counts are less than 100 (if more than 100, continue the flush).
3) Prepare particle standard: pipette approx. 1 ml of shaken particles into a blender filled with approx. 2 cups of DI water. Blend it. Pipette approx. 1 ml of diluted, blended particles into 50 ml of DI water.
4) Measure particle standard: pipette approx. 1 ml of double diluted standard into Accusizer bulb. Press the start measurement-Autodilution button. Confirm particles counts are more than 9200 by looking in the status bar. If counts are less than 9200, press stop and 10 inject more sample.
5) Immediately after measurement, inject one full pipette of soap (5% Micro 90) into bulb and press the Start Automatic Flush Cycles button.

(5) Test Method for Determining Median Volume-Weighted Particle Size of Microcapsules One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in deionized water to form a capsule slurry for characterization for particle size distribution.

The median volume-weighted particle size of the microcapsules is measured using an Accusizer 780A, made by Particle Sizing Systems, Santa Barbara Calif., or equivalent. The instrument is calibrated from 0 to 300 μm using particle size standards (as available from Duke/Thermo-Fisher-Scientific Inc., Waltham, Mass., USA). Samples for particle size evaluation are prepared by diluting about 1 g of capsule slurry in about 5 g of de-ionized water and further diluting about 1 g of this solution in about 25 g of water. About 1 g of the most dilute sample is added to the Accusizer and the testing initiated using the autodilution feature. The Accusizer should be reading in excess of 9200 counts/second. If the counts are less than 9200 additional sample should be added. Dilute the test sample until 9200 counts/second and then the evaluation should be initiated. After 2 minutes of testing the Accusizer will display the results, including the median volume-weighted particle size.

EXAMPLES

The following examples are given solely for the purpose of illustration and are not to be construed as limiting the invention, as many variations thereof are possible.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein. Some examples are provided below.

Example 1

Polyacrylate Microcapsule

Polyacrylate microcapsules having the characteristics displayed in Table 3 below were prepared.

TABLE 3

| Parameter | Description | Value |
|---|---|---|
| Wall material | Polyacrylate Shell | |
| Core Material | Isopropyl Myristate content of the core material (by weight of the microcapsule) | 10% |
| Actual Median Diameter(μm) | Volume weighted median diameter of the microcapsules | 13.1 μm |
| Core/Wall Ratio | Proportion of the mass of the core material to mass of the shell material | 70/30 |
| Fracture Strength | As determined by the Fracture Strength Test Method described herein. | 6.83 MPa |
| Core Material | Fragrance | 90% |

The polyacrylate microcapsule with the characteristics displayed in Table 3 may be prepared as follows. An oil solution, consisting of 112.34 g Fragrance Oil, 12.46 g isopropyl myristate, 2.57 g DuPont Vazo-67, 2.06 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.56 grams of tert-butyl amino ethyl methacrylate (Sigma Aldrich), 0.56 grams of beta-carboxy ethyl acrylate (Sigma Aldrich), and 46.23 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

Example 2

The polyacrylate microcapsules described in Table 3 above were included in Composition C at the indicated percentage and referred to as "Microcapsules". Compositions A, B, C, and D were included in separate dispensers. Alternatively, Composition A and Composition C may be stored in a first and second reservoir, respectively, in a dispenser having at least a first and second reservoir. Alternatively, Composition A and Composition D may be stored in a first and second reservoir, respectively, in a dispenser having at least a first and second reservoir.

| | (% w/w) |
|---|---|
| Composition A | |
| Ethanol (96%) | 74.88 |
| Fragrance | 14 |
| Water | 10.82 |
| Diethylamino Hydroxybenzol Hexyl Benzoate | 0.195 |
| Ethylhexyl Methoxycinnamate | 0.105 |
| Composition B | |
| Water | 99.35 |
| Phenoxyethanol | 0.3 |
| Trometamol | 0.25 |
| Disodium EDTA | 0.1 |
| Composition C | |
| Water | 92.5847 |
| Microcapsules of Example 1 | 6.0361 |
| Carbomer | 0.5018 |
| Phenoxyethanol | 0.2509 |
| Magnesium Chloride | 0.2456 |
| Sodium Hydroxide | 0.1254 |
| Disodium EDTA | 0.0836 |
| Polyvinyl alcohol | 0.0655 |
| Sodium Benzoate | 0.0409 |
| Potassium Sorbate | 0.0409 |
| Xanthan Gum | 0.0246 |
| Composition D | |
| Water | 91.0327 |
| Microcapsules of Example 2 | 7.4485 |
| Carbomer | 0.4771 |
| Phenoxyethanol | 0.2385 |
| Magnesium Chloride | 0.3074 |
| Sodium Hydroxide | 0.1193 |
| Disodium EDTA | 0.0795 |
| Polyvinyl alcohol | 0.1639 |
| Sodium Benzoate | 0.0512 |
| Potassium Sorbate | 0.0512 |
| Xanthan Gum | 0.0307 |

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dispenser comprising:
a first reservoir in liquid communication with a first pump;
a second reservoir in liquid communication with a second pump;
a swirl chamber;
at least one exit orifice; and
an actuator;
wherein the first pump is in liquid communication with said swirl chamber, which is in liquid communication with the at least one exit orifice;
wherein the second pump is in liquid communication with said swirl chamber, which is in liquid communication with the at least one exit orifice;
wherein said first and second pumps are in communication with the actuator;
wherein the first reservoir comprises a first composition, said first composition comprising a volatile solvent and a first fragrance;
wherein the second reservoir comprises a second composition, said second composition comprising a carrier and a plurality of microcapsules said microcapsules not exceeding, 10% by weight of said second composition;
wherein the at least one exit orifice dispenses a first dose of the first composition and a second dose of the second composition;
wherein the microcapsules have a volume weighted fracture strength from about 0.1 Mpa to about 25 Mpa, from about 0.5 Mpa to about 25 Mpa, from about 0.5 Mpa to about 20 Mpa, from about 0.5 Mpa to about 15 Mpa, from about 0.5 to about 10 Mpa, or from about 1.0 to about 8.0 Mpa; and
wherein the microcapsules have a median volume-weighted particle size of from about 2 microns to about 80 microns, from about 10 microns to about 30 microns, or from about 10 microns to about 20 microns.

2. The dispenser of claim 1, wherein the second composition further comprises a second fragrance encapsulated within at least some of the microcapsules.

3. The dispenser of claim 2, wherein the first fragrance and the second fragrance vary in chemical make-up.

4. The dispenser of claim 2, wherein the second fragrance has a ClogP of less than 4.5.

5. The dispenser of claim 2, wherein the microcapsules further comprise an oil soluble material that has a ClogP of 4.5 or greater.

6. The dispenser of claim 5, wherein the oil soluble material comprises a material selected from the group consisting of mono, di- and tri-esters of $C_4$-$C_{24}$ fatty acids and glycerine; isopropryl myristate; soybean oil; hexadecanoic acid; methyl ester; isododecane; and combinations thereof.

7. The dispenser of claim 5, wherein the microcapsules comprise a material selected from the group consisting of polyacrylates; polyethylenes; polyamides; polystyrenes; polyisoprenes; polycarbonates; polyesters; polyureas; polyurethanes; polyolefins; polysaccharides; epoxy resins; vinyl polymers; urea cross-linked with formaldehyde or 3lutaraldehyde; melamine cross-linked with formaldehyde; gelatin-polyphosphate coacervates optionally cross-linked with 4lutaraldehyde; gelatin-gum Arabic coacervates; cross-linked silicone fluids; polyamine reacted with polyisocyanates; acrylate monomers polymerized via free radical polymerization; silk; wool; gelatine; cellulose; proteins; and combinations thereof.

8. The dispenser of claim 5, wherein the microcapsules comprise a polyacrylate material.

9. The dispenser of claim 5, wherein the microcapsules comprise a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator.

10. The dispenser of claim 9, wherein said amine is a diethylaminoethyl methacrylate, dimethylaminoethyl methacrylate, or tertiarybutyl aminoethyl methacrylate.

11. The dispenser of claim 1, wherein the first composition and second composition are dispensed from the dispenser at a volume ratio of from about 10:1 to about 1:10, about 5:1 to about1:5, from about 3:1 to about 1:3, or from about 2:1 to about 1:1 of the first composition to the second composition.

12. The dispenser of claim 1, wherein the first dose and the second dose have a combined volume of from about 30 microliters to 300 microliters, from about 50 microliters to 140 microliters, or from about 70 microliters to 130 microliters.

13. The dispenser of claim 1, wherein the volatile solvent comprises ethanol.

14. A dispenser comprising:
a first reservoir in liquid communication with a first pump;
a second reservoir in liquid communication with a second pump;
a swirl chamber;
at least one exit orifice; and
an actuator;
wherein the first pump is in liquid communication with said swirl chamber which is in liquid communication with the at least one exit orifice;
wherein the second pump is in liquid communication with said swirl chamber which is in liquid communication with the at least one exit orifice;
wherein said first and second pumps are in communication with the actuator;
wherein the first reservoir comprises the first composition, the first composition comprising ethanol and a first fragrance;
wherein the second reservoir comprises the second composition, the second composition comprising water; a suspending agent; and a plurality of microcapsules comprising a polyacrylate, at least some of which encapsulate a second perfume which may be the same or different from the first perfume said microcapsules not exceeding 7% by weight of said second composition;
wherein the at least one exit orifice dispenses a dose of the first composition and a dose of the second composition at about the same time; and wherein the first composition and second composition are dispensed from the dispenser at a volume ratio of about 2:1 to about 1:1;

wherein the volume weighted fracture strength of the majority of microcapsules is from about 1.0 to about 8.0 Mpa; and wherein the median volume weight size of the microcapsules is about 10 to about 20 microns.

15. The dispenser of claim 14, wherein the first dose and the second dose have a combined volume of from about 30 microliters to 300 microliters, from about 50 microliters to 140 microliters, or from about 70 microliters to 130 microliters.

* * * * *